US011517710B2

(12) United States Patent
Sigmon, Jr. et al.

(10) Patent No.: US 11,517,710 B2
(45) Date of Patent: *Dec. 6, 2022

(54) METHODS, MEDICAL DEVICES AND KITS FOR MODIFYING THE LUMINAL PROFILE OF A BODY VESSEL

(71) Applicant: COOK MEDICAL TECHNOLOGIES LLC, Bloomington, IN (US)

(72) Inventors: John C. Sigmon, Jr., Winston-Salem, NC (US); Vihar Surti, Winston-Salem, NC (US)

(73) Assignee: Cook Medical Technologies LLC, Bloomington, IN (US)

(*) Notice: Subject to any disclaimer, the term of this patent is extended or adjusted under 35 U.S.C. 154(b) by 350 days.

This patent is subject to a terminal disclaimer.

(21) Appl. No.: 16/692,049

(22) Filed: Nov. 22, 2019

(65) Prior Publication Data
US 2020/0086079 A1 Mar. 19, 2020

Related U.S. Application Data

(63) Continuation of application No. 16/198,686, filed on Nov. 21, 2018, now Pat. No. 10,512,751, which is a
(Continued)

(51) Int. Cl.
*A61M 25/00* (2006.01)
*A61B 17/12* (2006.01)
(Continued)

(52) U.S. Cl.
CPC ....... *A61M 25/00* (2013.01); *A61B 17/12036* (2013.01); *A61B 17/12186* (2013.01);
(Continued)

(58) Field of Classification Search
CPC . A61F 2/06; A61F 2/07; A61M 25/00; A61M 2025/1052; A61B 17/12022
See application file for complete search history.

(56) References Cited

U.S. PATENT DOCUMENTS 3,783,868 A  1/1974  Bokros
4,218,782 A  8/1980  Rygg
(Continued)

FOREIGN PATENT DOCUMENTS

WO  WO1995022611  8/1995
WO  WO1996024661  8/1996
(Continued)

OTHER PUBLICATIONS

International Searching Authority, "International Preliminary Report on Patentability" for International application No. PCT/US2016/055979, dated Apr. 10, 2018, pp. 1-5.

*Primary Examiner* — Jason-Dennis N Stewart
(74) *Attorney, Agent, or Firm* — MacMillan, Sobanski & Todd, LLC

(57) ABSTRACT

Methods of modifying the luminal profile of a body vessel are described. An example method comprises advancing a cannula out of the distal end of a catheter disposed within the lumen of a body vessel of an animal and toward a target site on the wall of the body vessel; passing contrast dye through the cannula toward the target site; simultaneously continuing the advancing and passing until the distal end of the cannula punctures the inner layer of the wall of the body vessel at the target site; and passing a bulking agent through the cannula and into a space between connective tissue layers surrounding the vessel wall at the target site. Medical devices, medical device assemblies, and kits are also described.

20 Claims, 14 Drawing Sheets

Related U.S. Application Data continuation of application No. 15/288,201, filed on Oct. 7, 2016, now Pat. No. 10,173,027.

(60) Provisional application No. 62/238,265, filed on Oct. 7, 2015.

(51) Int. Cl.
*A61B 17/34* (2006.01)
*A61M 31/00* (2006.01)

(52) U.S. Cl.
CPC ..... *A61B 17/3478* (2013.01); *A61M 25/0084* (2013.01); *A61M 31/005* (2013.01); *A61B 17/12109* (2013.01); *A61M 25/0069* (2013.01); *A61M 2025/0018* (2013.01); *A61M 2025/0089* (2013.01)

(56) References Cited

U.S. PATENT DOCUMENTS

| | | | |
|---|---|---|---|
| 4,642,117 A | 2/1987 | Nguyen et al. |
| 4,902,508 A | 2/1990 | Badylak et al. |
| 4,956,178 A | 9/1990 | Badylak et al. |
| 5,002,071 A | 3/1991 | Harrell |
| 5,156,613 A | 10/1992 | Sawyer |
| 5,156,620 A | 10/1992 | Pigott |
| 5,275,826 A | 1/1994 | Badylak et al. |
| 5,411,552 A | 5/1995 | Andersen et al. |
| 5,476,471 A | 12/1995 | Shifrin et al. |
| 5,554,389 A | 9/1996 | Badylak et al. |
| 5,607,465 A | 3/1997 | Camilli |
| 5,711,969 A | 1/1998 | Patel et al. |
| 5,855,601 A | 1/1999 | Bessler et al. |
| 5,885,619 A | 3/1999 | Patel et al. |
| 5,955,110 A | 9/1999 | Patel et al. |
| 5,968,096 A | 10/1999 | Whitson et al. |
| 5,993,844 A | 11/1999 | Abraham et al. |
| 6,099,587 A | 8/2000 | Badylak et al. |
| 6,110,201 A | 8/2000 | Quijano et al. |
| 6,126,686 A | 10/2000 | Badylak et al. |
| 6,168,614 B1 | 1/2001 | Andersen et al. |
| 6,200,336 B1 | 3/2001 | Badylak et al. |
| 6,206,931 B1 | 3/2001 | Cook et al. |
| 6,264,992 B1 | 7/2001 | Voytik-Harbin et al. |
| 6,287,334 B1 | 9/2001 | Moll et al. |
| 6,299,637 B1 | 10/2001 | Shaolian et al. |
| 6,444,229 B2 | 9/2002 | Voytik-Harbin et al. |
| 6,485,723 B1 | 11/2002 | Badylak et al. |
| 6,508,833 B2 | 1/2003 | Pavcnik et al. |
| 6,527,800 B1 | 3/2003 | McGuckin et al. |
| 6,572,650 B1 | 6/2003 | Abraham et al. |
| 6,582,482 B2 | 6/2003 | Andersen et al. |
| 6,666,892 B2 | 12/2003 | Hiles et al. |
| 6,695,878 B2 | 2/2004 | McGuckin et al. |
| 6,716,241 B2 | 4/2004 | Wilder et al. |
| 6,752,828 B2 | 6/2004 | Thorton |
| 7,276,535 B1 | 10/2007 | Wang |
| 7,387,604 B2 | 6/2008 | Case et al. |
| 7,611,542 B2 | 11/2009 | Bourne et al. |
| 7,905,826 B2 | 3/2011 | Case et al. |
| 8,021,692 B2 | 9/2011 | Hiles et al. |
| 8,808,392 B2 | 8/2014 | Cook et al. |
| 8,834,351 B2 | 9/2014 | Case et al. |
| 2001/0011187 A1 | 8/2001 | Pavcnik et al. |
| 2001/0039450 A1 | 11/2001 | Pavcnik et al. |
| 2002/0123800 A1 | 9/2002 | Taheri et al. |
| 2002/0188348 A1 | 12/2002 | DiMatteo et al. |
| 2003/0026787 A1 | 2/2003 | Fearnot et al. |
| 2003/0036795 A1 | 2/2003 | Andersen et al. |
| 2003/0130726 A1 | 7/2003 | Thorpe et al. |
| 2003/0191525 A1 | 10/2003 | Thornton |
| 2003/0208261 A1 | 11/2003 | Thorpe et al. |
| 2004/0015230 A1 | 1/2004 | Moll et al. |
| 2004/0027557 A1 | 2/2004 | Caputo et al. |
| 2004/0049262 A1 | 3/2004 | Obermiller et al. |
| 2004/0193253 A1 | 9/2004 | Thorpe et al. |
| 2005/0222649 A1 | 1/2005 | Capuano et al. |
| 2005/0192235 A1 | 9/2005 | Hunter et al. |
| 2011/0319868 A1 | 12/2011 | Hiles et al. |
| 2012/0040012 A1 | 2/2012 | Girsh |
| 2014/0228933 A1 | 8/2014 | Case et al. |
| 2017/0100559 A1 | 4/2017 | Sigmon, Jr. et al. |

FOREIGN PATENT DOCUMENTS

| | | |
|---|---|---|
| WO | WO1996025179 | 8/1996 |
| WO | WO2000032112 | 6/2000 |
| WO | WO2001019285 | 3/2001 |
| WO | WO2003002165 | 1/2003 |
| WO | WO2003070124 | 8/2003 |

METHODS, MEDICAL DEVICES AND KITS FOR MODIFYING THE LUMINAL PROFILE OF A BODY VESSEL

CROSS-REFERENCE TO RELATED APPLICATION

This application is a continuation of U.S. application Ser. No. 16/198,686, filed on Nov. 21, 2018, which is a continuation of U.S. application Ser. No. 15/288,201, filed Oct. 7, 2016 and which claims the benefit of U.S. Provisional Application No. 62/238,265, filed Oct. 7, 2015. The entire contents of each of these related applications are hereby incorporated by reference into this disclosure.

FIELD

The disclosure relates generally to the field of medical devices, medical device assemblies, methods of use, and methods of treatment. More particularly, the disclosure relates to the introduction of an agent into the tissue of a wall of a body vessel to modify the luminal profile of the body vessel.

BACKGROUND

Body vessels, such as veins, arteries and other vessels, are prone to a variety of disorders and conditions for which modification of the luminal profile of the body vessel presents an opportunity for treatment. For example, the veins of the lower extremities contain venous valves that prevent blood from regurgitating back down the leg and help return blood to the heart. Each of these venous valves contains leaflets that coapt to provide valving action. Chronic Venous Insufficiency (CVI) can develop when one or more venous valves become incompetent, which can occur as a result of leaflets failing to coapt sufficiently. Once CVI develops, venous blood can pool in the lower leg, causing edema, varicose veins, pain and poor circulation.

Vein stripping and removal can be performed as treatment for venous insufficiency that occurs in superficial veins. For deep veins, however, the current standard treatment requires surgical intervention, such as valvuloplasty, vein transplantation or vein transposition.

Modifying the luminal profile of the body vessel at the location of an incompetent valve can increase or restore coaptation of leaflets in the valve. For example, if a body vessel has stretched or lost an ability to maintain valve leaflets in relative positions suitable for coaptation, a treatment that modifies the luminal profile of the body vessel can place the valve leaflets in relative positions suitable for coaptation to effectively restore valve function.

In one approach to modifying the luminal profile of a body vessel, referred to as 'bulking,' an agent is introduced into the layers of the wall of the body vessel. For example, U.S. Pat. No. 8,834,351 for METHOD OF MODIFYING VASCULAR VESSEL WALLS describes a bulking process in which a remodelable biomaterial is introduced into a wall of a body vessel of a patient's vasculature from a position within the lumen of the body vessel.

Modifying the luminal profile of an artery may prove beneficial in the treatment of arterial aneurysms and in the introduction of selective embolization. For example, modifying the luminal profile of an artery could be performed to reinforce the vessel wall of the artery at or near the site of an aneurysm. Also, modifying the luminal profile of an artery could be performed to a sufficient degree to achieve occlusion. This may provide a viable method for blocking blood flow to tumors or other cancerous regions.

Introducing a bulking agent to modify the luminal profile of a body vessel has proven challenging, though, and the art lacks specific methods and devices useful for accomplishing this promising, but delicate, treatment procedure. A need exists, therefore, for new and useful methods, medical devices and kits for modifying the luminal profile of a body vessel.

BRIEF SUMMARY OF SELECTED EXAMPLES

Methods of modifying the luminal profile of a body vessel are described. An example method comprises advancing a cannula out of the distal end of a catheter disposed within the lumen of a body vessel of an animal and toward a target site on the wall of the body vessel; passing contrast dye through the cannula toward the target site; simultaneously continuing the advancing and passing until the distal end of the cannula punctures the wall of the body vessel at the target site; and passing a bulking agent through the cannula and into a space between connective tissue layers surrounding the vessel wall at the target site.

Another example method comprises locating a position of a natural valve within a body vessel of an animal; advancing a cannula out of the distal end of a catheter disposed within the lumen of the body vessel and toward a target site on the wall of the body vessel and adjacent the natural valve; passing contrast dye through the cannula toward the target site; simultaneously continuing the advancing and passing until the distal end of the cannula punctures the wall of the body vessel at the target site; and passing bulking agent through the cannula and into a space between connective tissue layers surrounding the vessel wall at the target site.

Another example method comprises locating a position of a natural valve within a body vessel of an animal; measuring the inner diameter of the body vessel at the position of the natural valve; advancing a cannula out of the distal end of a catheter disposed within the lumen of the body vessel and toward a target site on the wall of the body vessel and adjacent the natural valve; passing contrast dye through the cannula toward the target site; simultaneously continuing the advancing and passing until the distal end of the cannula punctures the wall of the body vessel at the target site; passing bulking agent through the cannula and into a space between connective tissue layers surrounding the vessel wall at the target site; and measuring the inner diameter of the body vessel at the position of the natural valve.

Another example method comprises locating a position of a natural valve within a body vessel of an animal; measuring the inner diameter of the body vessel at the position of the natural valve to determine a first inner diameter value; advancing a cannula out of the distal end of a catheter disposed within the lumen of the body vessel and toward a target site on the wall of the body vessel and adjacent the natural valve; passing contrast dye through the cannula toward the target site; simultaneously continuing the advancing and passing until the distal end of the cannula punctures the wall of the body vessel at the target site; passing bulking agent through the cannula and into a space between connective tissue layers surrounding the vessel wall at the target site; measuring an inner diameter of the body vessel at the position of the natural valve to determine a second inner diameter value; comparing the first and second inner diameter values to determine a difference between the first and second inner diameter values; determining whether repetition of one or more of the steps of advancing, passing contrast dye and passing bulking agent is desired based on the difference between the first and second inner diameter values; and repeating one or more of the steps of advancing, passing contrast dye and passing bulking agent if desired.

Medical devices useful for modifying the luminal profile of a body vessel are also described. An example medical device comprises an elongate member defining an elongate member lumen extending between a proximal end defining a proximal opening and a distal end defining a distal opening; a cannula disposed within and axially movable within the elongate member lumen, and a seal disposed within and closing the distal opening. The cannula defines a cannula passageway extending between a cannula proximal end and a cannula distal end. The cannula distal end defines a cutting edge adapted to form a seal passageway through the seal and to puncture an inner layer of a body vessel wall. The seal is adapted to permit passage of the cannula distal end through the seal upon distally-directed axial movement of the cannula within the elongate member lumen.

Another example medical device comprises an elongate member defining an elongate member lumen extending between a proximal end defining a proximal opening and a distal end defining a distal opening; a cannula disposed within and axially movable within the elongate member lumen, and an elastomeric seal disposed within and closing the distal opening. The cannula defines a cannula passageway extending between a cannula proximal end and a cannula distal end. The cannula distal end defines a cutting edge adapted to form a seal passageway through the seal and to puncture an inner layer of a body vessel wall. The elastomeric seal is adapted to permit passage of the cannula distal end through the seal upon distally-directed axial movement of the cannula within the elongate member lumen. A distal surface of the elastomeric seal defines a plurality of protrusions.

Kits useful for modifying the luminal profile of a body vessel are also described. An example kit comprises a medical device comprising an elongate member defining an elongate member lumen extending between a proximal end defining a proximal opening and a distal end defining a distal opening; a cannula disposed within and axially movable within the elongate member lumen, and a seal disposed within and closing the distal opening. The example kit further comprises a first storage vessel containing contrast dye and adapted to be secured to the proximal end of the cannula and a second storage vessel containing a bulking agent and adapted to be secured to the proximal end of the cannula. Instructions for using the medical device and the first and second storage vessels together, such as instructions for performing a method according to an embodiment, can be included in a kit.

Additional understanding of these examples and the scope of the claimed invention can be obtained with review of the drawings and the detailed description of selected examples.

DETAILED DESCRIPTION OF SELECTED EXAMPLES

The following detailed description and the appended drawings describe and illustrate various example embodiments of medical devices that have a releasable member. In addition, example methods of treatment are described and illustrated. The description and illustration of these examples are provided to enable one skilled in the art to make and use a medical device and/or practice a method of use and/or method of treatment using a medical device. They are not intended to limit the scope of the claims in any manner.

The use of "e.g.," "etc.," "for instance," "in example," and "or" and grammatically related terms indicate non-exclusive alternatives without limitation, unless otherwise noted. The use of "optionally" and grammatically related terms means that the subsequently described element, event, feature, or circumstance may or may not be present or occur, and that the description includes instances where said element, event, feature, or circumstance occurs and instances where it does not. The use of "attached" refers to the fixed, releasable, or integrated association of two or more elements and/or devices. Thus, the term "attached" includes releasably attaching or fixedly attaching two or more elements and/or devices. As used herein, the terms "proximal" and "distal" are used to describe opposing axial ends of the particular element or feature being described. The use of "inner diameter" refers to the length of a straight line passing from a point on an inner surface of a tubular member, through a point on the longitudinal axis of the tubular member, and to an opposing or substantially opposing point on the inner surface of the tubular member. The term "body vessel" refers to any tubular vessel within the body of an animal, including, but not limited to, humans, and includes elongate passages. As examples, the term includes veins, arteries, ducts and other vessels. The term "animal" includes human and other mammals. The methods, medical devices and kits described herein are particularly well-suited for use in veins and arteries but can indeed be used in any suitable body vessel.

Figure 1:
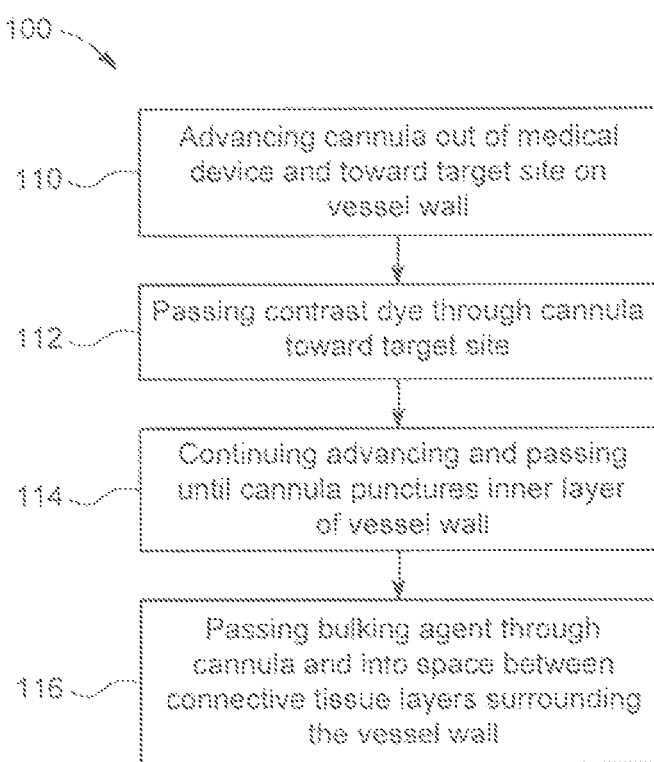
FIG. 1 is a flowchart representation of an example method.

FIG. 1 illustrates a flowchart representation of a first example method 100 of modifying the luminal profile of a body vessel of an animal. A step 110 of the method 100 comprises advancing a cannula out of the distal end of a medical device disposed within the lumen of the body vessel and toward a target site on the wall of the body vessel. Another step 112 comprises passing contrast dye through the cannula toward the target site. Another step 114 comprises continuing the advancing 110 and passing 112 until the cannula punctures the wall of the body vessel and the contrast dye begins to enter the space between connective tissue layers surrounding the wall of the body vessel. Another step 116 comprises passing a bulking agent through the cannula and into the space between connective tissue layers surrounding the vessel wall.

Any suitable medical device can be used in the performance of the method 100, including the example catheters described herein. The medical device need only have an element that defines a lumen within which the cannula can be disposed and axially moved to achieve the desired advancing as described herein. Examples of suitable medical devices include conventional catheters and the example catheters according to embodiments of the invention described herein. Furthermore, any suitable cannula can be used as a component of or with the medical device in the performance of the method 100. The cannula need only define a passageway suitable for the passage of the contrast dye and bulking agent through the cannula and define structure for puncturing the inner layer of the wall of the body vessel for which the method is being performed. Examples of suitable cannula include convention cannulae used with catheters and the example cannulae according to embodiments of the invention described herein.

Before initiating the method 100, such as immediately before performing the step 110 of advancing the cannula, suitable preparatory actions can be included and performed as part of a method according to a particular embodiment. For example, a step of attaching one or more storage vessels containing appropriate fluids or other materials suitable for use in the treatment being administered, such as contrast dye, bulking agent, or another fluid or material, can be performed as part of the method according to an embodiment. Also, a step of navigating the distal end of the catheter through the body vessel until the distal end is disposed adjacent the target site on the vessel wall or otherwise within a distance of the target site that is traversable by the cannula as described when advanced distally out of the catheter can be included.

The step 112 of passing contrast dye through the cannula toward the target site can be performed in any suitable manner, including conventional techniques for passing fluid through an inner component of a catheter. For example, a storage vessel containing contrast dye can be attached to the proximal end of the cannula, or other component of the medical device that is in fluid communication with the cannula passageway, and pressure can be applied onto the contrast dye to force some of the contrast dye out of the storage vessel, into the cannula passageway and out of the distal end of the cannula into the environment external to the medical device. A conventional syringe with appropriate fittings, such as Luer-type fittings, is suitable for the storage vessel in this regard. It is noted that any suitable visualization agent that facilitates visualization of the location of an injection can be used in this step, and contrast dye is merely an example. A skilled artisan will be able to select a suitable visualization agent for use in a method according to a particular example based on various considerations, including the nature and location of the body vessel for which modification of the luminal profile is desired and the nature of any visualization devices and/or equipment being used during performance of the method. Other examples of suitable visualization agents include all agents visible under fluoroscopy and all agents visible under ultrasound.

It is considered important to perform the step 112 of passing contrast dye through the cannula toward the target site while the step 110 of advancing the cannula toward the target site is being performed. Thus, the method 100 requires a continuing 114 of the advancing 110 and passing 112 steps until the cannula punctures an inner layer of the vessel wall without passing through the entire thickness of the vessel wall. This continuing 114 can be performed in any suitable manner, such as by distally advancing the cannula while maintaining a constant or substantially constant position of an outer elongate tubular member of the medical device and while applying pressure to a fluid column of contrast dye contained within the cannula passageway, such as by applying pressure to a syringe or other storage vessel in fluid communication with the cannula passageway. This is considered important because it facilitates visualization of the transition of the distal end of the cannula during movement from a position within the lumen of the body vessel to one within the space between connective tissue layers surrounding the vessel wall. Being able to visualize this positional transition, in turn, facilitates proper positioning prior to initiation of the step 116 of passing a bulking agent through the cannula and into the space between connective tissue layers surrounding the vessel wall, as well as any additional steps of passing agent(s) into this space, as described in detail below. Without performing the passing 112 while the advancing 110 is being performed, the inventors have determined that visualization of proper positioning prior to initiation of the step 116 of passing a bulking agent through the cannula and into the space between connective tissue layers surrounding the vessel wall is difficult and the possibility of the need for multiple wall punctures increases, which is not desirable. Thus, in all methods, the advancing 110 and passing 112 are performed simultaneously at least until the cannula punctures an inner layer of the vessel wall without passing through the entire thickness of the vessel wall.

The step 116 of passing bulking agent through the cannula and into the space between connective tissue layers surrounding the vessel wall can be performed in any suitable manner, including conventional techniques for passing fluid through an inner component of a catheter. For example, a storage vessel containing a suitable bulking agent can be attached to the proximal end of the cannula, or other component of the medical device that is in fluid communication with the cannula passageway, and pressure can be applied onto the bulking agent to force some of the bulking agent out of the storage vessel, into the cannula passageway and out of the distal end of the cannula into the environment external to the medical device. A conventional syringe with appropriate fittings, such as Luer-type fittings, is suitable for the storage vessel in this regard.

As an alternative to or in addition to step 116 of passing bulking agent through the cannula and into the space between connective tissue layers surrounding the vessel wall, a step of passing bulking agent through the cannula and into the space between layers of the vessel wall of the body vessel can be included in a particular method. Inclusion of such a step, either as an alternative or in addition to step 116, can facilitate and potentially enhance the modification of the luminal profile of the body vessel.

Before initiating the step 116 of passing bulking agent through the cannula and into the space between connective tissue layers surrounding the vessel wall, such as immediately after the continuing 114 the advancing 110 and passing 112 is performed until the cannula punctures an inner layer of the vessel wall without passing through the entire thickness of the vessel wall, suitable preparatory actions can be included and performed as part of a method according to a particular embodiment. For example, a step of attaching one or more storage vessels containing a bulking agent, can be performed as part of the method according to an embodiment. Also, a step of disconnecting a storage vessel containing the contrast dye can be included and performed as part of a method according to a particular embodiment. It is noted, though, that a storage vessel containing contrast dye and a storage vessel containing a bulking agent can be attached to the cannula, or otherwise in fluid communication with the cannula passageway, at the same time, if desired.

In all methods, medical devices and kits, any suitable bulking agent can be used. Examples of suitable types of bulking agents include liquids, gels, foams, fluidized biomaterials, and other materials. Viscous liquids are considered suitable for use as a bulking agent. Viscous liquids having an injection viscosity of between about 1 and about 1,000,000 cP in a cannula ranging between about 18 to about 35 gauge are considered particularly well-suited for use as a bulking agent in the inventive methods, medical devices, and kits. The inventors have determined that viscous liquids having an injection viscosity of between about 50,000 and about 200,000 cP in a cannula ranging between about 23 to about 27 gauge are considered particularly well-suited for use as a bulking agent in the inventive methods, medical devices, and kits, particularly when being used to alter the luminal profile of an animal vein near a natural venous valve. Carboxymethyl cellulose hydrogel and alginate is considered particularly well-suited for use as a bulking agent in the inventive methods, medical devices and kits. A hydrogel containing between about 4% alginate and about 30% alginate is considered particularly advantageous for use as a bulking agent. Indeed, the inventors have determined that a hydrogel containing about 17.5% alginate is particularly advantageous for use as a bulking agent. As described below, a crosslinking agent can also be included with the bulking agent. The inclusion of an electrolyte in the bulking agent is also considered advantageous, particularly with gel-based bulking agents, at least because the presence of the electrolyte facilitates water retention and increases the time during which the bulking agent remains in the target site to accomplish the desired modification of the luminal profile of the relevant body vessel. If included in the bulking agent, any suitable electrolyte can be used. The inclusion of a salt, such as $MgCl_2$, is considered advantageous. Inclusion of a salt in the bulking agent, such as $MgCl_2$, at a concentration of between about 1 mol/L and about 6 mol/L is considered particularly advantageous.

In all methods, medical devices and kits, any suitable bulking agent can be used that is paired with one or more crosslinking agents. Addition of a crosslinking agent can allow the bulking agent to undergo a phase change and/or increase the bulking agent's viscosity above its injection viscosity. Crosslinking of the bulking agent could occur via electrostatic or covalent crosslinking. Example electrostatic crosslinkers include but are not limited to ligand-receptor interactions, such as streptavidin-biotin interactions, or ionic interactions from molecules containing divalent and trivalent elements, such as $MgCl_2$, $CaCl_2$, $SrCl_2$, $BaCl_2$, $Al_3SO_4$, $BaSO_4$, $CaCO_3$, Ferric chloride, and Ferrous chloride. The inventors have determined that $SrCl_2$, particularly well-suited for use as a crosslinking agent in the methods, devices and kits described herein. The inventors have determined that the inclusion of $SrCl_2$ at a concentration of between about 0.05 Molar and about 4.00 Molar is particularly advantageous. Indeed, the inventors have determined that the inclusion of $SrCl_2$ at a concentration of about 0.33 Molar is particularly advantageous. Covalent crosslinking could be achieved by inclusion of a free radical generator, click chemistry, Schiff base reactions, and enzyme-mediated reactions. Additionally, stimuli-responsive bulking agents can be used that contain component(s) that trigger the crosslinking process, for example by light activation (added photoinitiator), temperature activation, or pH activation (added acid or base). It is considered advantageous for the crosslinked bulking agent to have a compressive modulus of 10 to 3000 kPa, preferably 100 to 500 kPa.

When a crosslinking agent is included, interaction between the crosslinking agent and the bulking agent can occur before or after the bulking agent is delivered to the target location. When the bulking and crosslinking agent interact before they are delivered to the target location, it is considered advantageous to have delayed crosslinking to facilitate delivery of the bulking agent. If delayed crosslinking is used, it is advantageous to maintain an injection viscosity of between about 1 and about 1,000,000 cP for the time required to deliver the combined bulking and crosslinking agent to the target location. When the bulking and crosslinking agent interact after they are delivered to the target location (i.e., in-situ crosslinking) the bulking and crosslinking agent can be delivered with a single or separate delivery that occurs simultaneously or sequentially. If single delivery is used, a dual beveled needle with a dual lumen catheter can be used to separate the bulking and crosslinking agent in the medical device used for delivery. If separate delivery of the bulking and crosslinking agent is used, the same delivery device can deliver each agent sequentially or each agent can be delivered with a separate delivery device simultaneously or sequentially. If sequential delivery of the bulking agent and crosslinking agent is performed, a suitable buffer may be used to add a layer that separates the agents within the delivery lumen of the cannula. If included, the buffer may be a gel that does not interact with the crosslinker, a suitable liquid, such as saline, phosphate saline buffer, or water, or any other suitable buffer.

A skilled artisan will be able to select a suitable bulking agent for use in a method, medical device and/or kit according to a particular embodiment based on various considerations, such as the nature of the body vessel being targeted and the degree to which the luminal profile is desired to be modified. The inventors have determined that the viscosity of a material is a predominant guiding criteria in the selection of a bulking agent at least because a relatively viscous liquid exhibits an ability to push against the inner layer of the wall of the body vessel once it has been injected into the space between connective tissue layers surrounding the vessel wall while also spreading circumferentially around the target site, essentially encircling the target site, instead of spreading longitudinally along the body vessel. The inventors have determined that the viscosity ranges listed above provide effective viscosities for use in the modification of the luminal profile of animal veins.

Figure 2A:
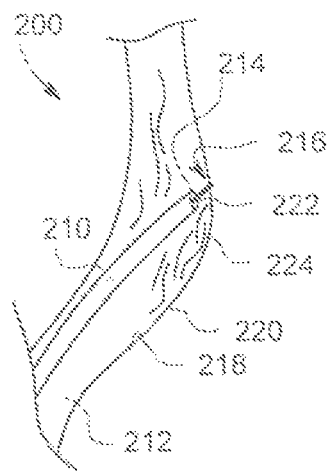
FIG. 2A is a schematic illustration of a portion of a body vessel within which the method illustrated in FIG. 1 is being performed.
Figure 2B:
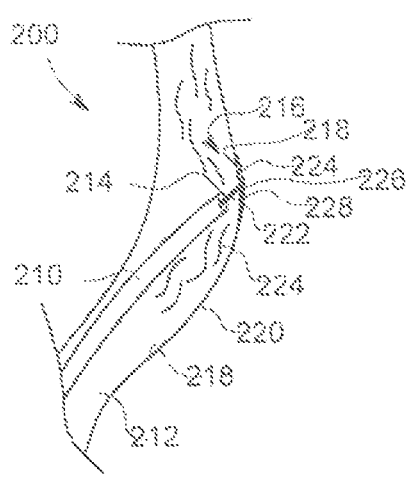
FIG. 2B is another schematic illustration of a portion of a body vessel within which the method illustrated in FIG. 1 is being performed.
Figure 2C:
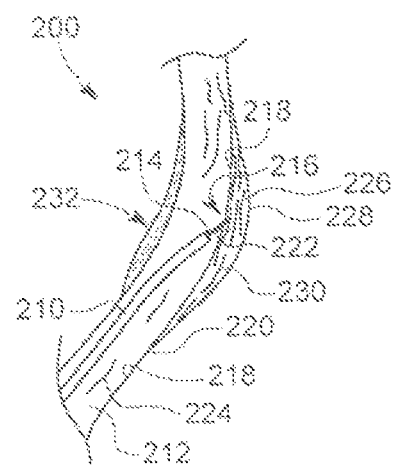
FIG. 2C is another schematic illustration of a portion of a body vessel within which the method illustrated in FIG. 1 is being performed.

Each of FIGS. 2A, 2B and 2C illustrates a portion of a body vessel 200 within which the example method 100 is being performed. In FIG. 2A, a catheter 210 has been navigated through the lumen 212 of the body vessel 200 to place the distal end 214 of the catheter 210 near a target site 216 on the inner layer 218 of the wall 220 of the body vessel 200. A cannula 222 has been advanced out of the distal end of the catheter 210 and toward the target site 216 on the wall 220 of the body vessel 200. Also, contrast dye 224 is being passed through the cannula 222 and toward the target site as the cannula 222 continues to be advanced out of the distal end of the catheter 210 and toward the target site 216 on the wall 220 of the body vessel 200. Because the cannula 222 has not yet contacted or punctured the inner layer 218 of the wall 220 of the body vessel 200, the contrast dye 224 dissipates in the lumen 212 of the body vessel 200.

In FIG. 2B, the cannula 222 has punctured the inner layer 218 of the wall 220 of the body vessel 200 and has passed through the wall 220 of the body vessel 200 and into the connective tissue layers surrounding the body vessel 200. As such, a small amount of contrast dye 224 has entered the space 226 between the inner layer 218 and another layer 228 of the connective tissue surrounding the wall 220 of the body vessel 200. At this point, someone performing the method 100 can perform any suitable and/or desirable preparatory steps for stopping the passing of contrast dye and initiating the passing of bulking agent through the cannula 222. For example, a step of disconnecting a storage vessel containing the contrast dye can be performed followed by a step of attaching one or more storage vessels containing a bulking agent.

In FIG. 2C, bulking agent 230 has been passed through the cannula 222 and into the space 226 between an inner layer 218 and another layer 228 of the connective tissue surrounding the wall 220 of the body vessel 200. As a result, the relatively thick bulking agent 230 spreads locally around the target site 216 to create a bulked region 232 of the body vessel 200. Within the bulked region 232, the inner diameter of the lumen 212 of the body vessel 200 has been reduced in comparison to the inner diameter of the lumen 212 of the body vessel 200 at the location of the bulked region 232 prior to the passing of the bulking agent 230 into the space 226 between the inner layer 218 and another layer 228 of the wall 220 of the body vessel 200. This can be visualized by comparing FIG. 2C to each of FIGS. 2A and 2B. The cannula 222 and catheter 210 can be withdrawn from the space 226 and lumen 212 using convention catheter and minimally-invasive techniques.

Figure 3:
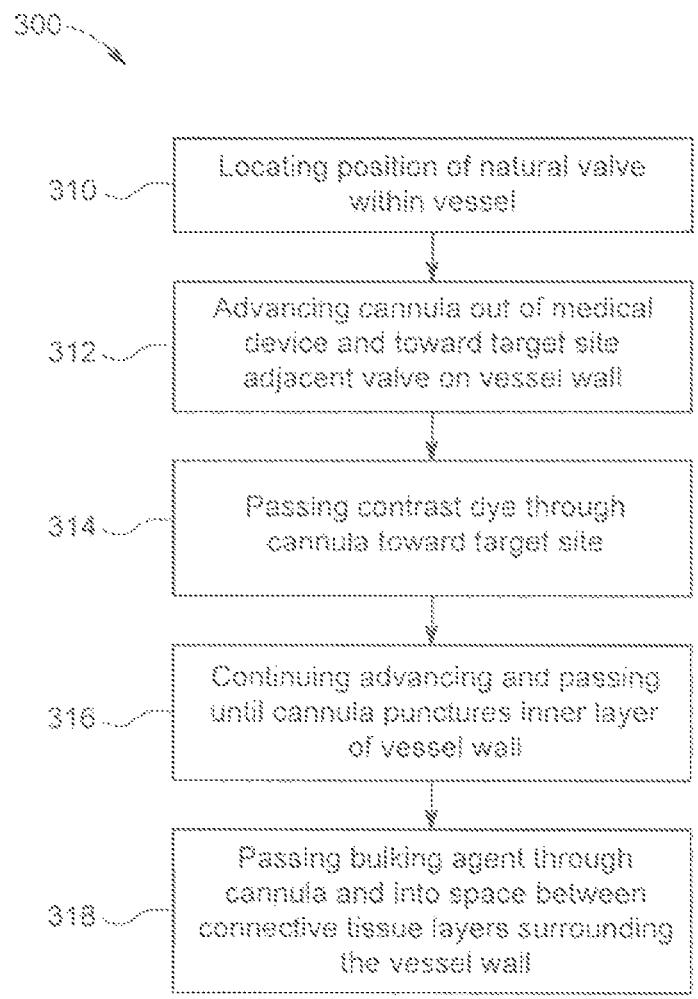
FIG. 3 is a flowchart representation of another example method.

As the methods result in a modification of the luminal profile of a body vessel, the methods can be used to treat valves within body vessels that have reduced or no coaptation due to separation of the leaflets of the valve. FIG. 3 illustrates a flowchart representation of another example method 300 of modifying the luminal profile of a body vessel of an animal. This method 300 is useful in the treatment of valves that have lost valving function or that have reduced valving function. A step 310 of the method 300 comprises locating the position of a natural valve within a body vessel. Another step 312 comprises advancing a cannula out of the distal end of a medical device disposed within the lumen of the body vessel and toward a target site on the wall of the body vessel that is adjacent the valve located in step 310. Another step 314 comprises passing contrast dye through the cannula toward the target site. Another step 316 comprises continuing the advancing 312 and passing 314 until the cannula punctures an inner layer of the wall of the body vessel and the contrast dye begins to enter the space between connective tissue layers surrounding the wall of the body vessel. Another step 318 comprises passing a bulking agent through the cannula and into the space between layers of the wall of the body vessel.

In this method 300, steps 312, 314, 316, and 318 are similar to the same steps described above for method 100. The step 310 of locating the position of a natural valve can be performed in any suitable and/or desirable manner and using any suitable and/or desirable technique, device, method, and/or equipment. For example, a natural venous valve can be located using conventional fluoroscopy visualization equipment and techniques.

It is noted that the methods described herein, including method 300, can be used with any suitable natural valve, such as venous valves, heart valves, and any other natural valve located within an animal, such as a human.

Figure 4:
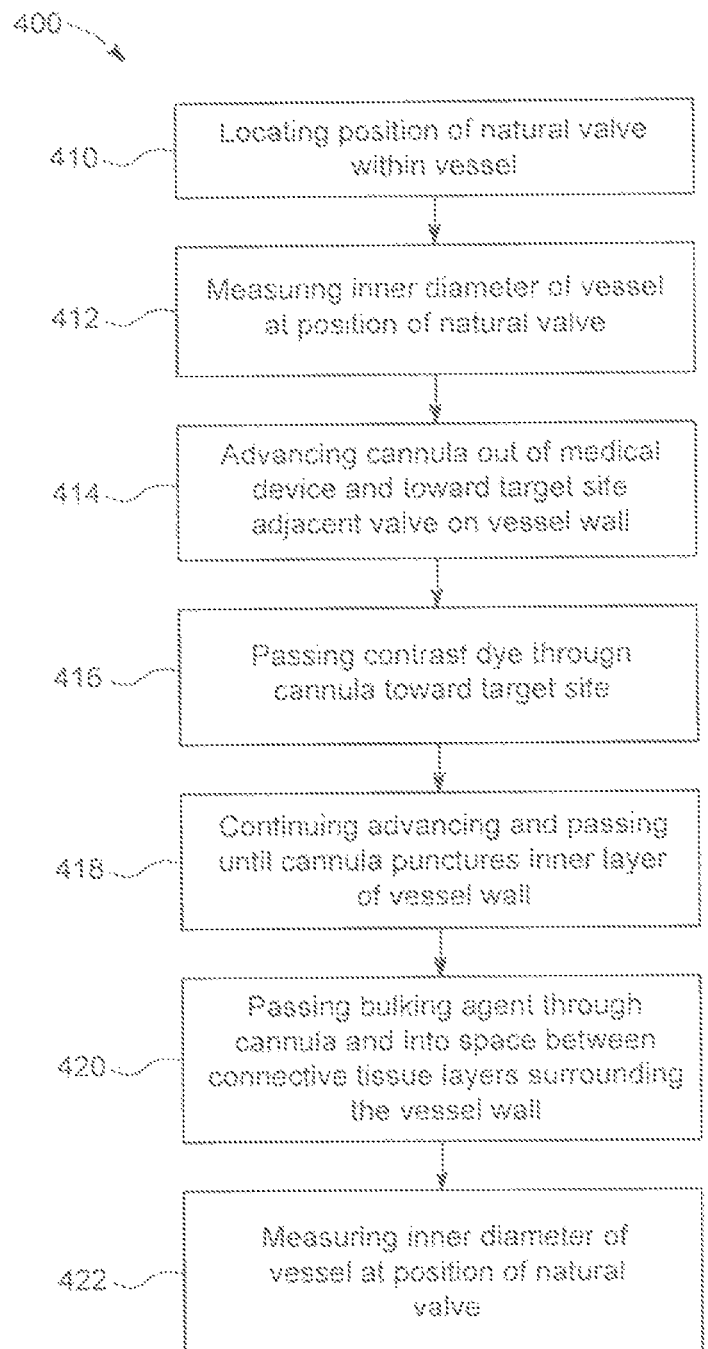
FIG. 4 is a flowchart representation of another example method.

It may be desirable to confirm that the luminal profile of a body vessel has been modified following performance of a method described herein. If so, modification of the luminal profile of a body vessel can be confirmed in any suitable and/or desirable manner and using any suitable and/or desirable technique, device, method and/or equipment. FIG. 4 illustrates a flowchart representation of another example method 400 of modifying the luminal profile of a body vessel of an animal that includes steps that enable such confirmation.

A step 410 of the method 400 comprises locating the position of a natural valve within a body vessel. Another step 412 comprises measuring the inner diameter of the body vessel at the position of the natural valve located in step 410. Another step 414 comprises advancing a cannula out of the distal end of a medical device disposed within the lumen of the body vessel and toward a target site on the wall of the body vessel that is adjacent the valve located in step 410. Another step 416 comprises passing contrast dye through the cannula toward the target site. Another step 418 comprises continuing the advancing 414 and passing 416 until the cannula punctures the wall of the body vessel and the contrast dye begins to enter the space between connective tissue layers surrounding the wall of the body vessel. Another step 420 comprises passing a bulking agent through the cannula and into the space between connective tissue layers surrounding the wall of the body vessel. Another step 422 comprises measuring the inner diameter of the body vessel at the position of the natural valve located in step 410 after performing the step 420 of passing a bulking agent through the cannula and into the space between the connective tissue layers of the wall of the body vessel.

In this method, steps 414, 416, 418, and 420 are similar to the same steps described above for method 100. The step 410 of locating the position of a natural valve is similar to the same step describe above for method 300. The steps 412 and 422, each of which requires measuring the inner diameter of the body vessel at a location of the located natural valve, can be performed in any suitable and/or desirable manner and using any suitable and/or desirable technique, device, method, and/or equipment. For example, a natural venous valve can be measured using conventional processes and techniques with infrared visualization equipment and techniques. It is noted that the steps 412, 422 can be performed in the same or different manner and using the same or different technique, device, method, and/or equipment.

Another example method comprises guiding an injection needle through a percutaneous access sheath and through an introducer to the desired location within a body vessel. Another step comprises simultaneously injecting contrast or another radiopaque fluid while advancing the needle through a wall at the desired location within the body vessel and into the connective tissue that surrounds the wall. Another step comprises visually observing the contrast or other radiopaque liquid spreading through the connective to confirm that the needle has reached a proper depth. Another step comprises locking the needle in place to secure the position at which the needle has the proper depth. At this point, additional volume of the radiopaque fluid can continue to fill the connective tissue surrounding the vessel wall, allowing an individual performing the method the visually observe and/or determine the thickness of the connective tissue surrounding the vessel; the thickness of the vessel wall by flushing contrast through the vessel and then measuring the distance between the inner diameter of the vessel and the nearest location of the radiopaque fluid to the inner diameter; the presence of fibrosis; the presence of a fistula between a neighboring organ; and/or the presence of an anastomosis between a neighboring vessel, among others.

If the individual is trying to gain access with a wire or a device from one vessel to a neighboring vessel by crossing through two vessel walls and the connective tissue that divides the two, the information gained by performance of an inventive method can provide the individual with the necessary information to facilitate crossing or to pursue an alternate route. In addition, by having radiopaque fluid filling the connective tissue between the two vessels, the individual can better direct a wire or device through fluoroscopic guidance by minimizing the risk of missing the target vessel.

In all methods, a crosslinking agent can be introduced in addition to the bulking agent. Thus, an additional step of passing a crosslinking agent through the cannula and into the space between connective tissue layers of the wall of the body vessel. Alternatively, a crosslinking agent can be included with the contrast dye used in the method, with the bulking agent used in the method, or both. For example, a crosslinking agent can be included in the contrast dye used in step 314 of method 300. Similarly, a crosslinking agent can be included in the contrast dye used in step 112 of method 100. Also similarly, a crosslinking agent can be included in the contrast dye used in step 416 and of method 400. Alternatively, a crosslinking agent can be introduced as a separate agent to the target location before, during, or after the bulking agent is delivered. For example, a step of passing a crosslinking agent through the cannula and into the space between connective tissue layers of the wall of the body vessel can be included before, during, or after step 318 is performed in method 300. Similarly, a step of passing a crosslinking agent through the cannula and into the space between connective tissue layers of the wall of the body vessel can be included before, during, or after step 116 is performed in method 100. Also similarly, a step of passing a crosslinking agent through the cannula and into the space between connective tissue layers of the wall of the body vessel can be included before, during, or after step 420 is performed in method 400. Alternatively, a delayed crosslinking agent can be introduced to the bulking agent before, during, or after steps 318, 116, and 420 in methods 300, 100, and 400, respectively.

Figure 5:
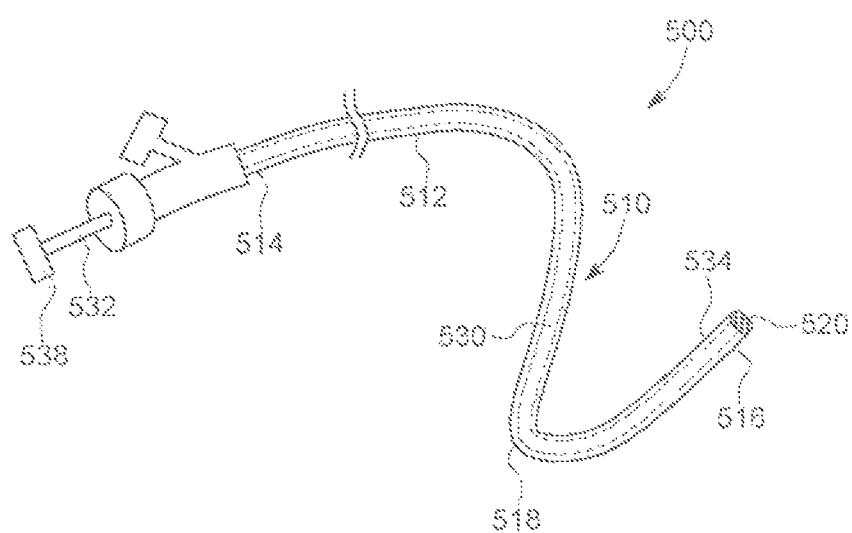
FIG. 5 is a perspective view of an example medical device.
Figure 5A:
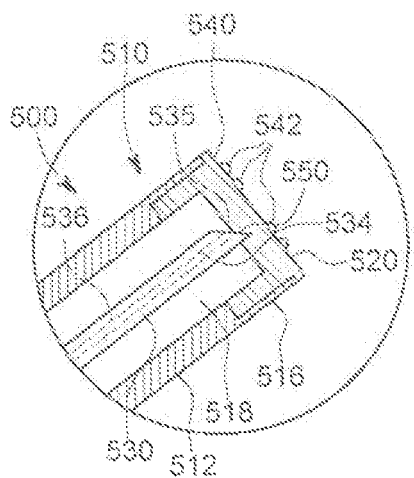
FIG. 5A is a magnified view of the distal end of the medical device illustrated in FIG. 5. The cannula is illustrated in a first, non-extended position.
Figure 5B:
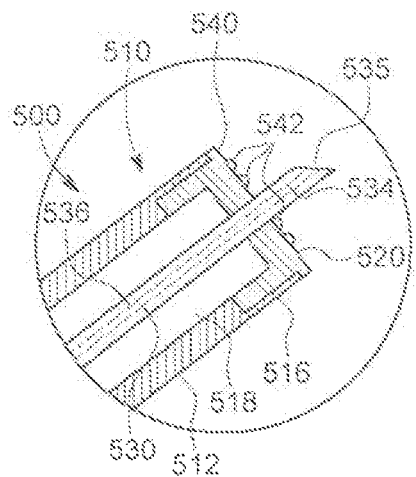
FIG. 5B is a magnified view of the distal end of the medical device illustrated in FIG. 5. The cannula is illustrated in a second, extended position.

FIGS. 5, 5A and 5B illustrate an example medical device 500 suitable for use in the inventive methods. The medical device 500 is a catheter 510 that has an outer tubular member 512 that extends between outer tubular member proximal 514 and outer tubular member distal 516 ends. The outer tubular member 512 defines a lumen 518. A seal 520 is disposed on the distal end 516 of the outer tubular member 512 and blocks communication between the lumen 518 and the external environment.

A cannula 530 is disposed within the lumen 518 of the outer tubular member 512. The cannula 530 has a cannula proximal end 532 and a cannula distal end 534 and defines a cannula lumen 536 that extends between the cannula proximal end 532 and a cannula distal end 534. The connector 538, such as a Luer lock or other suitable fitting, is attached to the cannula proximal end 532. The cannula distal end 534 defines a cutting edge 540, similar to a needle.

The seal 520 can be any suitable member that can be secured to the distal end 516 of the outer tubular member 512 and allow the distal end of the cannula 530 to pierce the seal and pass through an opening created by such piercing. An examples of a suitable seal is, but is not limited to, an elastomeric member secured to the distal end 516 of the outer tubular member 512 with adhesive, as best illustrated in FIGS. 5A and 5B. In this embodiment, the seal 520 includes an outer surface 540 that defines a plurality of protrusions 542 that extend outwardly from the outer surface 540. In this embodiment, the plurality of protrusions is integrally formed by the seal 520 and, as described in detail below, can aid in maintaining the medical device 500 in contact with an inner wall of a body vessel during performance of a method.

While the outer tubular member 512 has been illustrated as having a particular structural arrangement, an outer tubular member can have any suitable structural arrangement. Skilled artisans will be able to select a suitable structural arrangement for an outer tubular member according to a particular embodiment based on various considerations, including the structural arrangement of a cannula being used and/or the nature of the body vessel within which the medical device is intended to be used. Similarly, a cannula can have any suitable structural arrangement.

The outer tubular member 512 can be formed of any suitable material. Skilled artisans will be able to select a suitable material to form an outer tubular member according to a particular embodiment based on various considerations, including the material(s) that forms a cannula included in a medical device of which the outer tubular member is a component. Example materials considered suitable to form an elongate member include biocompatible materials, materials that can be made biocompatible, metals such as stainless steel, titanium, nickel-titanium alloy (e.g., Nitinol), thermoplastics, polymers, Pebax (Pebax is a registered trademark of Ato Chimie Corporation of Allee des Vosges, Courbevoie, France), nylon, polyethylene, high-density polyethylene (HDPE), high-performance polyethylene (HPPE), polyurethane, silicone, acrylonitrile butadiene styrene (ABS), polyoxymethylene (e.g., acetal), and any other material considered suitable for a particular application. In the illustrated embodiment, the elongate member 512 is formed of high-density polyethylene (HDPE).

Similarly, the cannula 530 can be formed of any suitable material. Skilled artisans will be able to select a suitable material to form a cannula according to a particular embodiment based on various considerations, including the material(s) that forms an outer tubular member included in a medical device of which the cannula is a component. Example materials considered suitable to form a cannula include biocompatible materials, materials that can be made biocompatible, metals such as stainless steel, titanium, nickel-titanium alloy (e.g., Nitinol), thermoplastics, polymers, Pebax (Pebax is a registered trademark of Ato Chimie Corporation of Allee des Vosges, Courbevoie, France), nylon, polyethylene, high-density polyethylene (HDPE), high-performance polyethylene (HPPE), polyurethane, silicone, acrylonitrile butadiene styrene (ABS), polyoxymethylene (e.g., acetal), and any other material considered suitable for a particular application. In the illustrated embodiment, the cannula 530 is formed of stainless steel.

Figure 6A:
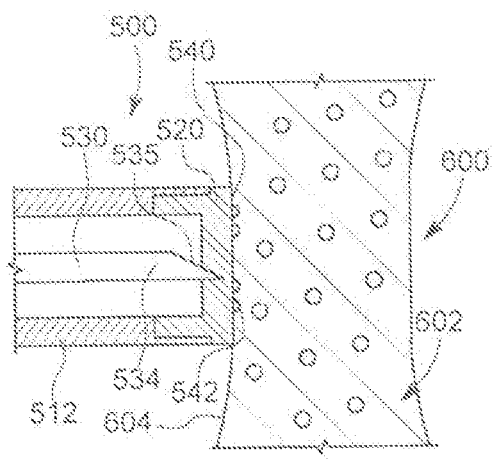
FIG. 6A is a schematic illustration of a portion of a body vessel within which the medical device illustrated in FIG. 5 is disposed and within which the method illustrated in FIG. 1 is being performed. The cannula of the medical device is illustrated in a first, non-extended position.
Figure 6B:
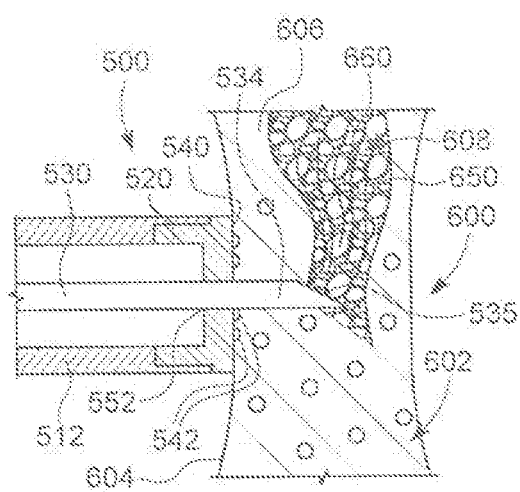
FIG. 6B is a schematic illustration of a portion of a body vessel within which the medical device illustrated in FIG. 5 is disposed and within which the method illustrated in FIG. 1 is being performed. The cannula of the medical device is illustrated in a second, extended position.
Figure 6C:
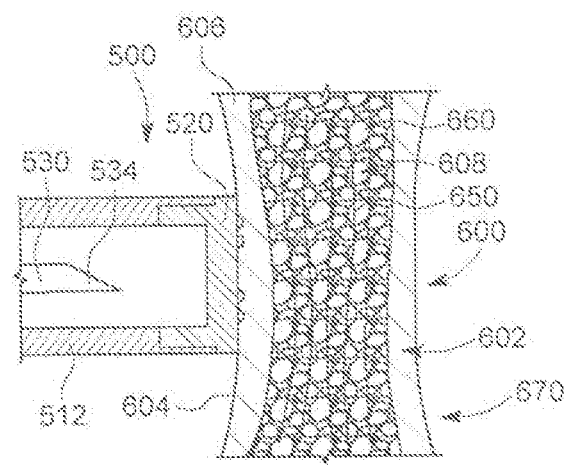
FIG. 6C is a schematic illustration of a portion of a body vessel within which the medical device illustrated in FIG. 5 is disposed and within which the method illustrated in FIG. 1 is being performed. The cannula of the medical device is illustrated in a third, retracted position.

Each of FIGS. 6A, 6B and 6C is a schematic illustration of a portion of a body vessel 600 within which the medical device 500 illustrated in FIGS. 5, 5A and 5B is disposed and within which the method 100 illustrated in FIG. 1 is being performed.

In FIG. 6A, the cannula 530 of the medical device 500 is illustrated in a first, non-extended position. In this position, the cannula distal end 534 is fully contained within the outer tubular member 512. Also a portion of the cutting edge 540 is seated within a pre-formed notch 550 defined by the seal 520. The outer surface 540 and the plurality of protrusions 542 on the seal 520 are in contact with the inner surface 604 of the vessel wall 602 of the body vessel. In this Figure, the advancing step 110 of method 100 has not yet been initiated.

In FIG. 6B, the cannula 530 of the medical device 500 is illustrated in a second, extended position. In this position, the cannula distal end 534 has pierced and extended through an opening 552 that it formed in the seal 520. The cannula distal end 534 has punctured the inner layer 606 of the vessel wall 602. Furthermore, contrast dye 650 and bulking agent 660 have been passed through the cannula 520 and into the space 608 between connective tissue layers surrounding the vessel wall 602.

In FIG. 6C, the cannula 530 of the medical device 500 is illustrated in a third, retracted position. In this position, the cannula distal end 534 has been retracted back through the opening it formed in the seal 520 and pulled into the lumen 518 defined by the outer tubular member 512. Contrast dye 650 and bulking agent 660 remain in the space 608 between connective tissue layers surrounding the vessel wall 602, with sufficient bulking agent 650 present to formed a bulked region 670 in the body vessel.

Figure 7:
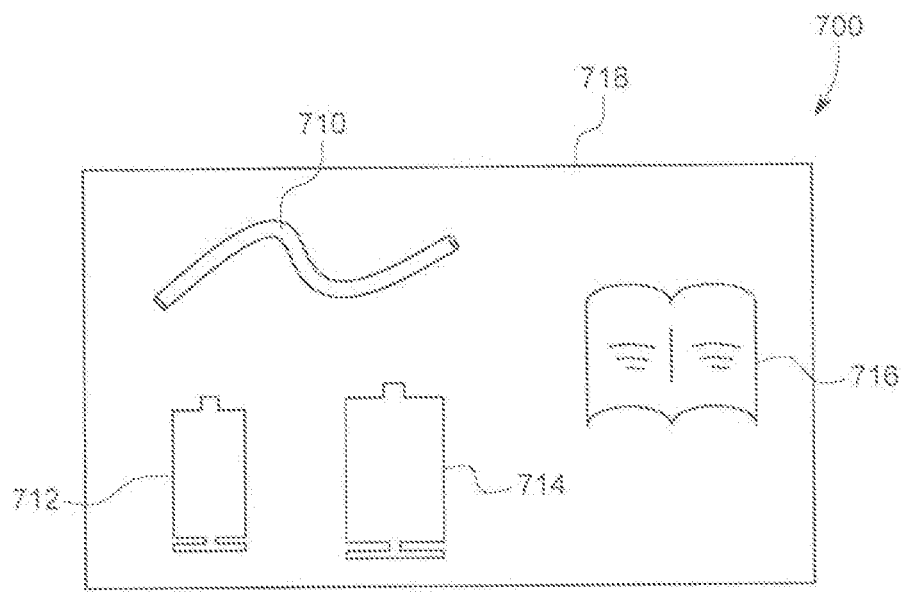
FIG. 7 is a schematic representation of an example kit.

FIG. 7 is a schematic illustration of an example kit 600 useful for modifying the luminal profile of a body vessel. The kit includes a medical device 610 according to an embodiment, such as one of the examples described herein. Also, the kit 600 includes a first storage vessel 612 containing contrast dye and adapted to be secured to a portion of the medical device, such as the proximal end of a cannula component of the medical device 610. Also, the kit 600 includes a second storage vessel 614 containing a bulking agent and adapted to be secured to a portion of the medical device 610, such as the proximal end of a cannula component of the medical device 610. The illustrated example kit 600 also includes instructional information, such as printed material 616 describing a method according to an embodiment, such as one of the example methods described herein. The instructional information could also comprise pre-recorded media, such as a video on a recordable media, or an address where such information can be obtained, such as an Internet URL. The kit 600 also includes an outer container 618 within which all other components are packaged.

Kits according to embodiments can include additional optional components. For example, as described in detail above, it may be desirable to include a crosslinking agent in the performance of an inventive method. Accordingly, a kit according to an embodiment can include an additional storage vessel containing a crosslinking agent and adapted to be secured to a portion of the medical device, such as the proximal end of a cannula component of the medical device 610. Also, as described above, it may be desirable to include a buffer in the performance of an inventive method. Accordingly, a kit according to an embodiment can include an additional storage vessel containing a buffer and adapted to be secured to a portion of the medical device, such as the proximal end of a cannula component of the medical device 610. Also as described in detail above, it may be desirable to include a crosslinking agent with another element used in the performance of an inventive method. For example, a crosslinking agent can be mixed with a contrast dye, a buffer, and/or a bulking agent. Accordingly, a kit according to an embodiment can include a storage vessel containing a crosslinking agent mixed with a contrast dye, a buffer, and/or a bulking agent and adapted to be secured to a portion of the medical device, such as the proximal end of a cannula component of the medical device 610. Indeed, a kit according to an embodiment can include one or more of a storage vessel containing a crosslinking agent mixed with a contrast dye, a storage vessel containing a crosslinking agent mixed with a buffer, and a storage vessel containing a crosslinking agent mixed with a bulking agent. Each of these storage vessel(s) can be adapted to be secured to a portion of the medical device, such as the proximal end of a cannula component of the medical device 610.

Figure 8:
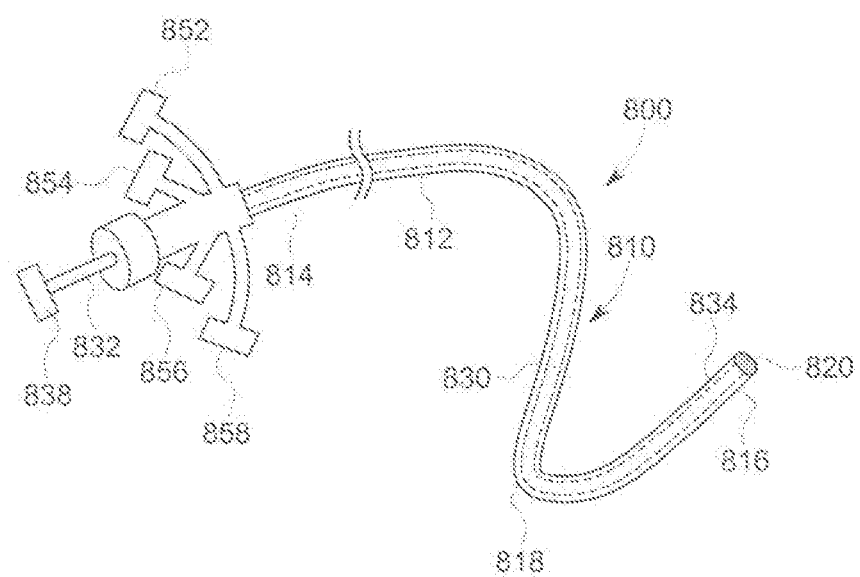
FIG. 8 is a perspective view of another example medical device.

FIG. 8 illustrates another example medical device 800 suitable for use in the inventive methods. The medical device 800 is a catheter 810 that has an outer tubular member 812 that extends between outer tubular member proximal 814 and outer tubular member distal 816 ends. The outer tubular member 812 defines a lumen 818. A seal 820 is disposed on the distal end 516 of the outer tubular member 512 and blocks communication between the lumen 518 and the external environment. A cannula 830 is disposed within the lumen 818 of the outer tubular member 812. The cannula 830 has a cannula proximal end 832 and a cannula distal end 834 and defines a cannula lumen 836 that extends between the cannula proximal end 832 and a cannula distal end 834. A connector 838, such as a Luer lock or other suitable fitting, is attached to the cannula proximal end 832. The cannula distal end 834 defines a cutting edge 840, similar to a needle.

In this embodiment, the medical device 800 includes four connectors 852, 854, 856, 858, each of which defines a passageway that is in fluid communication with the cannula lumen 836 and defines a suitable fitting for connecting a storage vessel, such as a syringe or other suitable storage vessel, to the medical device 800. The medical device 800 is particularly well-suited for use in inventive methods described herein, including methods that include the use of a buffer and a crosslinking agent, as it provides the ability to deliver these various agents through the cannula by selective forcing of fluid through the connectors 852, 854, 856, 858, either sequentially, simultaneously, or in any desired combination or order. For example, in one embodiment, four separate storage vessels can be attached to the medical device 800 using the connectors to form a medical device assembly that includes the medical device 800 and attached storage vessels. One storage vessel can include contrast dye; one storage vessel can include crosslinking agent; one storage vessel can include buffer; one storage vessel can include bulking agent. Also, as noted above, storage vessels can be used that include mixtures of one or more of the various elements used in the inventive methods. For example, a storage vessel containing a crosslinking agent mixed with contrast dye can be attached to the medical device 800 using one of the connectors 852, 854, 856, 858 in the assembling of a medical device assembly. Also, it is noted that two or more of the various elements used in the inventive methods can be contained within a single storage vessel and separated for sequential delivery through one of the connectors and into the cannula lumen 836 during performance of an inventive method. For example, in one embodiment, a buffer can be stored separately within a storage vessel with a bulking agent, such as in separate layers. A medical device assembly can be assembled by attaching this storage vessel to the medical device 800, and attaching other suitable storage vessels for the contrast dye and crosslinking agent, if desired.

While the illustrated medical device includes four connectors 852, 854, 856, 858, a medical device according to an embodiment can have a number of connectors that corresponds to a number of storage vessels containing elements for use in an inventive method. For example, a medical device can have one, two, three or four connectors.

EXAMPLES

Figure 9A:
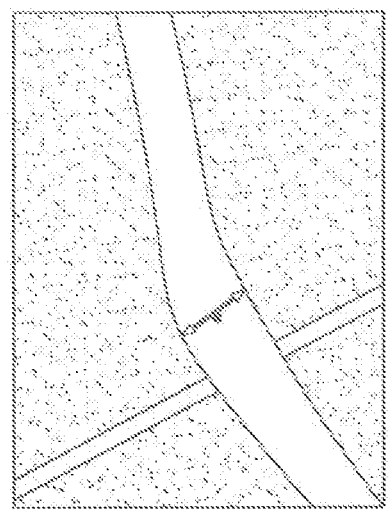
FIG. 9A is a schematic illustration of an animal vein during a stage of luminal modification.
Figure 9B:
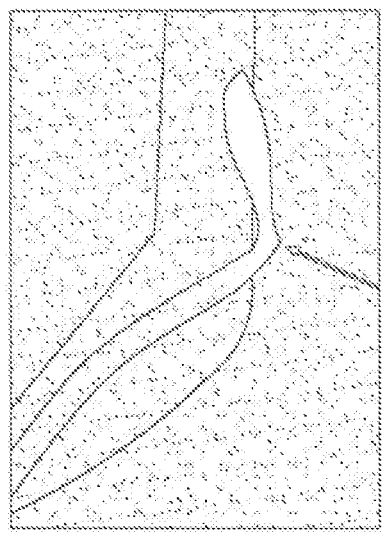
FIG. 9B is a schematic illustration of an animal vein during another stage of luminal modification.
Figure 9C:
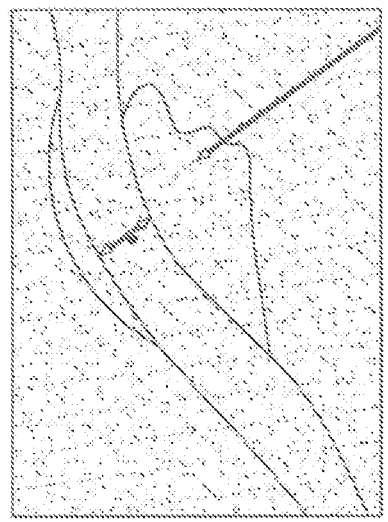
FIG. 9C is a schematic illustration of an animal vein during another stage of luminal modification.

FIGS. 9A, 9B and 9C are schematic illustrations of an animal vein during various stages of luminal modification in accordance with an inventive method.

In FIG. 9A, the inner diameter of the body vessel is measured at the position of a previously-located natural venous valve, indicated by the double-headed arrow, while under visualization.

In FIG. 9B, a cannula, an injection needle in this example, has been advanced through a guide catheter to the target site. The cannula has been advanced toward the target site while simultaneously injecting contrast dye until the cannula has punctured the inner layer of the wall of the body vessel. This is evident from the small amount of contrast dye in the lumen of the body vessel and the contrast dye located in the space between layers of the wall of the body vessel, indicated by the arrow.

In FIG. 9C, the inner diameter of the body vessel is measured at the position of the previously-located natural venous valve while under visualization. The bulking agent has been passed through the cannula and into the space between layers of the wall of the body vessel, indicated by the arrow, and the cannula and its catheter have been removed from the body vessel. As is evident from a comparison of FIG. 9A and FIG. 9C, the inner diameter of the body vessel has been reduced by approximately 40% at the position of the natural venous valve.

Figure 10:
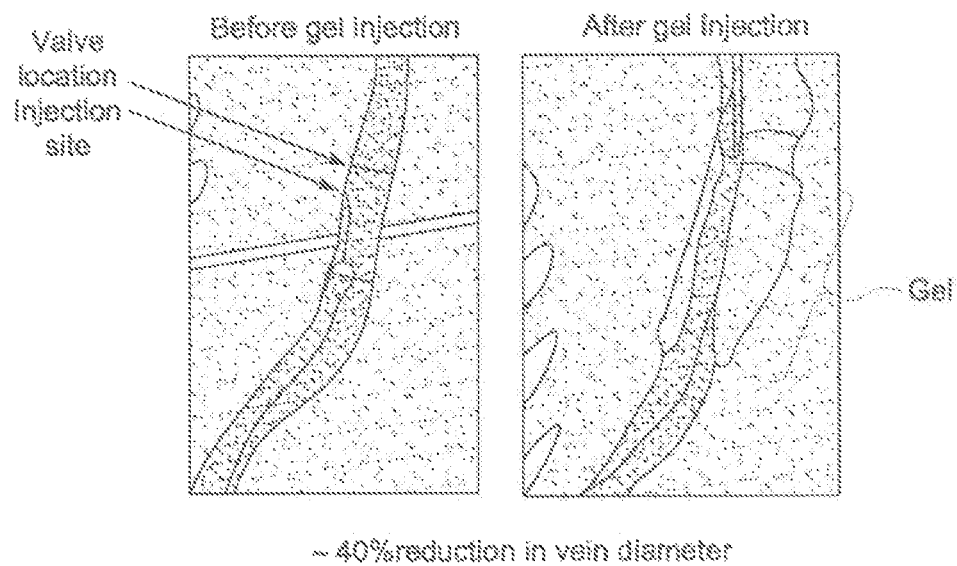
FIG. 10 includes two fluoroscopic images of an external jugular vein of a pig. The left panel shows the vein before injection of bulking agent. The right panel shows the vein after injection of bulking agent.

FIG. 10 includes two fluoroscopic images of an external jugular vein of a pig. The left panel shows the vein before injection of a bulking agent. The right panel shows the vein after injection of a gel bulking agent in accordance with a method described herein.

The vein illustrated in FIG. 10 includes a natural valve, the location of which is identified in the left panel. The injection site located below the valve location in illustration is also identified in the left panel. The bulking agent, labeled 'Gel', is evident in the right panel in the area adjacent the vein.

As is evident by comparing the right panel to the left panel, the vein diameter was reduced by ~40% following performance of the method.

Figure 11:
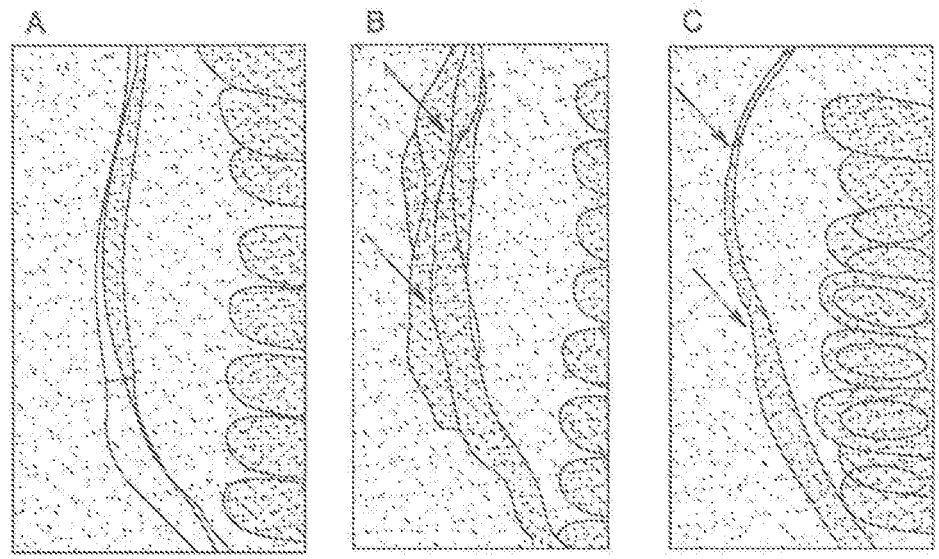
FIG. 11 includes three fluoroscopic images of an external jugular vein of a pig. Panel A shows the vein before injection of bulking agent and crosslinking agent. Panel B shows the vein after injection of bulking agent and crosslinking agent. Panel C shows the vein one week after treatment

FIG. 11 includes three fluoroscopic images of an external jugular vein of a pig. Panel A shows the vein before injection of bulking agent and crosslinking agent. Panel B shows the vein after injection of bulking agent and crosslinking agent. Panel C shows the vein one week after treatment.

In this example, a bulking agent comprising 17.5% alginate was delivered to each of two target sites in the vein in accordance with a method described herein. Also as part of this method, a crosslinking agent comprising 0.33M $SrCL_2$ was delivered to each of the two target sites. The locations of the two target sites are indicated by the arrows in Panel B and Panel C. The presence of the bulking agent and crosslinking agent is evident in Panel B in the area adjacent the vein.

Panel C shows the vein one week after injection of the bulking and crosslinking agent and demonstrates the durability of the bulked area and its lasting impact on the diameter of the body vessel.

Figure 12:
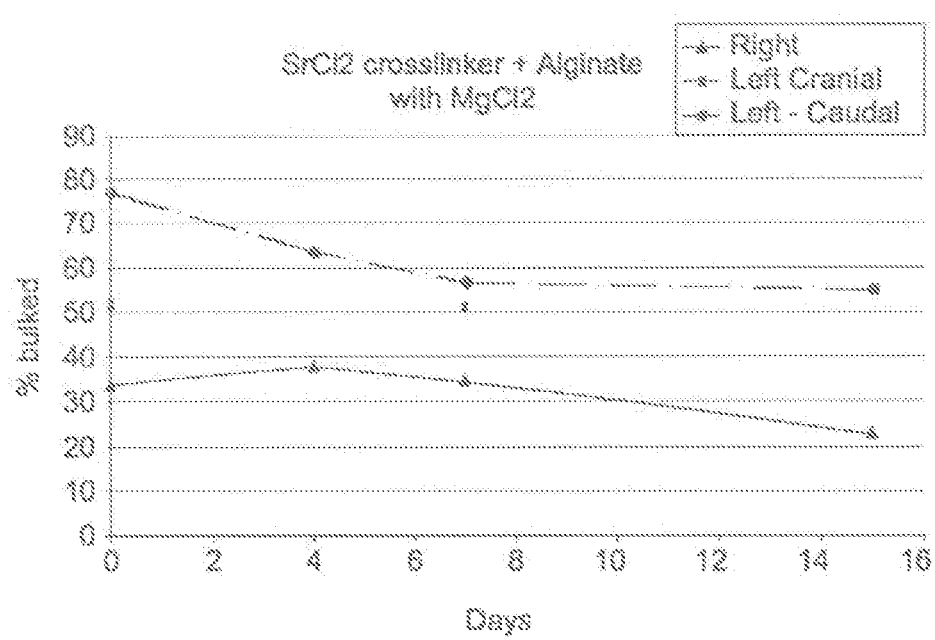
FIG. 12 is a graph of experimental results and shows a calculated percent bulked value as a function of time.

FIG. 12 is a graph of experimental results following delivery of bulking and crosslinking agents in accordance with a method described herein. The graph illustrates a calculated percent bulked value as a function of time and demonstrates sustained bulking over a two week survival in the external jugular veins of pigs. The percent bulked values were calculated as a comparison of the bulked diameter to the native vessel diameter. Note that Day 0 venogram measurements for the percent bulked calculations were taken immediately after delivery of crosslinking and bulking agents. Note also that the left cranial location was only measured successfully on day 0 and day 7.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. A method of modifying the luminal profile of a body vessel at a target site, comprising:
    passing a bulking agent through a cannula and into a space between connective tissue layers surrounding a wall of said body vessel at said target site; and
    passing a cross-linking agent through a cannula and into the space between connective tissue layers surrounding the wall of said body vessel at said target site.

2. The method of claim 1, wherein the bulking agent comprising a hydrogel.

3. The method of claim 2, wherein the hydrogel contains alginate.

4. The method of claim 3, wherein the hydrogel comprises between about 4% and about 30% alginate.

5. The method of claim 3, wherein the hydrogel comprises about 17.5% alginate.

6. The method of claim 1, wherein the bulking agent comprises about 17.5% alginate.

7. The method of claim 1, wherein the crosslinking agent comprises a salt.

8. The method of claim 7, wherein the crosslinking agent is selected from the group consisting of MgCl2, CaCl2, SrCl2, BaCl2, Al3SO4, BaSO4, CaCO3, ferric chloride, and ferrous chloride.

9. The method of claim 7, wherein the crosslinking agent comprises SrCl2.

10. The method of claim 7, wherein the crosslinking agent has a concentration of between about 0.05 Molar and about 4.00 Molar.

11. The method of claim 7, wherein the crosslinking agent has a concentration of about 0.33 Molar.

12. A method of modifying the luminal profile of a body vessel at a target site, comprising:
    passing a bulking agent through a cannula and into a space between connective tissue layers surrounding a wall of said body vessel at said target site; and
    passing a cross-linking agent through a cannula and into the space between connective tissue layers surrounding the wall of said body vessel at said target site;
    wherein the bulking agent and the cross-linking agent are sequentially passed through the same cannula.

13. The method of claim 12, further comprising passing a buffer through the cannula between passing the bulking agent through the cannula and passing the cross-linking agent through the cannula.

14. The method of claim 13, wherein the buffer is selected from the group consisting of a gel that does not interact with the cross-linking agent, saline, phosphate saline buffer, and water.

15. The method of claim 1, wherein said body vessel comprises a vein.

16. A method of modifying the luminal profile of a body vessel at a target site, comprising:
    passing a bulking agent through a cannula and into a space between connective tissue layers surrounding a wall of said body vessel at said target site, the bulking agent comprising a hydrogel containing alginate; and
    passing a cross-linking agent through a cannula and into the space between connective tissue layers surrounding the wall of said body vessel at said target site, the cross-linking agent selected from the group consisting of MgCl2, CaCl2, SrCl2, BaCl2, Al3SO4, BaSO4, CaCO3, ferric chloride, and ferrous chloride.

17. The method of claim 16, wherein the hydrogel comprises between about 4% and about 30% alginate.

18. The method of claim 16, wherein the hydrogel comprises about 10% alginate.

19. The method of claim 16, wherein said body vessel comprises a vein.

20. A method of modifying the luminal profile of a body vessel at a target site, comprising:
    sequentially passing a bulking agent and a cross-linking agent through a cannula and into a space between connective tissue layers surrounding a wall of said body vessel at said target site;
    wherein the bulking agent comprises a hydrogel containing between about 4% and about 30% alginate; and
    wherein the cross-linking agent comprises SrCl2 and having a concentration of between about 0.05 Molar and about 4.00 Molar.

* * * * *